United States Patent
Marat et al.

(10) Patent No.: US 10,457,619 B2
(45) Date of Patent: Oct. 29, 2019

(54) RESORCINOL DERIVATIVES FOR COSMETIC USE THEREOF

(71) Applicant: L'OREAL, Paris (FR)

(72) Inventors: Xavier Marat, Aulnay-sous-Bois (FR); Amélie Gueguiniat, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/061,913

(22) PCT Filed: Dec. 8, 2016

(86) PCT No.: PCT/EP2016/080237
§ 371 (c)(1),
(2) Date: Jun. 13, 2018

(87) PCT Pub. No.: WO2017/102536
PCT Pub. Date: Jun. 22, 2017

(65) Prior Publication Data
US 2018/0370886 A1    Dec. 27, 2018

(30) Foreign Application Priority Data
Dec. 16, 2015 (FR) .................. 15 62542

(51) Int. Cl.
| C07C 39/11 | (2006.01) |
| C07C 69/18 | (2006.01) |
| A61Q 19/02 | (2006.01) |
| A61K 8/34 | (2006.01) |
| A61K 8/37 | (2006.01) |

(52) U.S. Cl.
CPC .............. *C07C 39/11* (2013.01); *A61K 8/347* (2013.01); *A61K 8/375* (2013.01); *A61Q 19/02* (2013.01); *C07C 69/18* (2013.01)

(58) Field of Classification Search
CPC ....... C07C 39/11; C07C 69/18; C07C 69/017; A61Q 19/02; A61K 8/375; A61K 8/347
See application file for complete search history.

(56) References Cited

U.S. PATENT DOCUMENTS 7,300,646 B2 * 11/2007 Harichian ............. A61K 8/365
424/400

FOREIGN PATENT DOCUMENTS

| JP | 2007186445 A | 7/2007 |
| WO | 2005/085169 A1 | 9/2005 |

OTHER PUBLICATIONS

Hoefnagel, A. et al., "Synthesis of 7-hydroxycoumarins Catalysed by Solid Acid Catalysts," J. Chem. Soc. Chem. Commun., 1995, pp. 225-226.

Kolancilar, H., "Synthesis of 7-Hydroxy-4-methylcoumarin Using Polyaniline/Montmorillonite K10 Composite as Catalyst," Asian Journal of Chemistry, vol. 22, No. 7, (2010) pp. 5694-5698.

Laufer, M.C. et al., "Synthesis of 7-hydroxycoumarins by Pechmann Reaction Using Nafion Resin/Silica Nanocomposites as Catalysts," J. Of Catalysis, 2003, 218, pp. 315-320.

Regnier, M. et al., "Keratinocyte-melanocyte co-cultures and Pigmented Reconstructed Human Epidermis: Models to Study Modulation of Melanogenesis," Pigment Reconstruction Epidermis Standard Study Model, Cellular and Molecular Biology, 1999, 45, 7, pp. 969-980.

International Search Report for Application No. PCT/EP2016/080237, dated Jan. 3, 2017.

* cited by examiner

*Primary Examiner* — Rosalynd A Keys
(74) *Attorney, Agent, or Firm* — The Marbury Law Group, PLLC

(57) ABSTRACT

The present invention relates to a compound of formula (I), in particular for the use thereof for depigmenting, lightening and/or bleaching the skin. (I) In which $R_1$ and $R_2$, which may be identical or different, denote hydrogen, or a COR5 radical in which R5 denotes a linear $C_1$-$C_{10}$ or branched $C_3$-$C_{10}$ alkyl radical, preferably a linear $C_1$-$C_6$ or branched $C_3$-$C_6$ alkyl radical, more preferentially a linear $C_1$-$C_4$ alkyl radical, $R_3$ denotes a linear $C_1$-$C_6$ or branched $C_3$-$C_6$ alkyl radical, preferably a linear $C_1$-$C_4$ or branched $C_3$-$C_4$ alkyl radical, and $R_4$ denotes H, a linear $C_1$-$C_6$ or branched $C_3$-$C_6$ alkyl radical, or a COR5 radical, and also the salts thereof, the solvates thereof and the optical isomers thereof, and the racemic mixtures thereof, alone or as a mixture. The present invention also relates to the novel compounds (I) and also to the process for preparing same and to a cosmetic process for depigmenting the skin using such compounds (I).

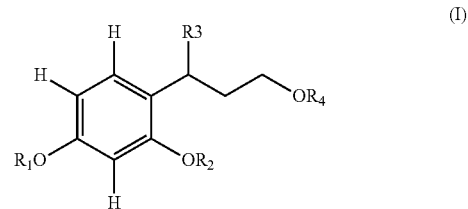

(I)

20 Claims, No Drawings

RESORCINOL DERIVATIVES FOR COSMETIC USE THEREOF

CROSS REFERENCE TO RELATED APPLICATIONS

This is a national stage application of PCT/EP2016/080237, filed internationally on Dec. 8, 2016, which claims priority to French Application No. 1562542, filed on Dec. 16, 2015, both of which are incorporated by reference herein in their entireties.

The present invention relates to the cosmetic use of resorcinol-based compounds for depigmenting and/or bleaching the skin, and also to certain novel resorcinol-based compounds.

At various periods in their life, some people develop darker and/or more colored blemishes on their skin, and more especially on the hands and the face, which give the skin heterogeneity. These blemishes are especially due to a high concentration of melanin in the keratinocytes located at the surface of the skin.

The use of highly effective inoffensive topical depigmenting substances is most particularly sought for the purpose of treating pigmentary blemishes.

The mechanism of formation of the pigmentation of the skin, i.e. of the formation of melanin, is particularly complex and involves, schematically, the following main steps:

Tyrosine→Dopa→Dopaquinone→Dopachrome→Melanin

Tyrosinase (monophenol dihydroxyl phenylalanine: oxygen oxidoreductase EC 1.14.18.1) is the essential enzyme involved in this sequence of reactions. In particular, it catalyzes the conversion reaction of tyrosine to give dopa (dihydroxyphenylalanine), by virtue of its hydroxylase activity, and the conversion reaction of dopa to give dopaquinone, by virtue of its oxidase activity. This tyrosinase acts only when it is in mature form under the effect of certain biological factors.

A substance is acknowledged as being depigmenting if it acts directly on the vitality of the epidermal melanocytes where melanogenesis takes place, and/or if it interferes with one of the steps of melanin biosynthesis, either by inhibiting one of the enzymes involved in melanogenesis, or by inserting itself as a structural analogue of one of the chemical compounds of the melanin synthesis chain, which chain can then be blocked, thus ensuring depigmentation.

Arbutin and kojic acid are known as skin depigmenting agents.

Substances with efficient depigmenting action, especially better than that of arbutin and kojic acid, have been sought.

However, there is still a need for a novel bleaching agent for human skin, whose action is as efficient as the known agents, but which does not have their drawbacks, i.e. which is nonirritant, nontoxic and/or nonallergenic to the skin, while at the same time being stable in a composition, or alternatively which has a reinforced action so as to be able to be used in lower amount, which considerably reduces the side effects observed.

In this regard, the Applicant has discovered, surprisingly and unexpectedly, that certain resorcinol compounds have good depigmenting activity, even at low concentration, without showing any cytotoxicity.

In this regard, the Applicant has discovered, surprisingly and unexpectedly, that certain resorcinol-based compounds have good depigmenting activity, even at low concentration.

Certain resorcinol-based compounds are already known in the prior art for their depigmenting activity. In this regard, mention may be made in particular of JP 2007186445 from Kuraray.

One subject of the invention is compounds of formula (I) as defined below for their dermatological use for depigmenting the skin.

A subject of the invention is also novel compounds of formula (II) as defined below.

A subject of the invention is also a nontherapeutic cosmetic treatment process for depigmenting, lightening and/or bleaching keratin materials, especially the skin, comprising the application to the skin of at least one compound of formula (I) as defined below.

A subject of the invention is also a composition comprising, in a physiologically acceptable medium, at least one compound of formula (II) as defined below.

A subject of the invention is also a nontherapeutic cosmetic process for depigmenting, lightening and/or bleaching keratin materials, especially the skin, comprising the application of the composition described previously.

More preferably, it is the process for depigmenting, lightening and/or bleaching the skin.

The invention also relates to the nontherapeutic cosmetic use of at least one compound of formula (I) as defined below, as an agent for bleaching, lightening and/or depigmenting keratin materials, especially the skin.

The compounds in accordance with the invention, i.e. in particular of formula (I) or of formula (II) as defined below, make it possible to depigment and/or lighten efficiently, or even bleach, human skin. They are especially intended to be applied to the skin of individuals bearing brownish pigmentation blemishes or liver spots, or to the skin of individuals wishing to combat the appearance of a brownish color caused by melanogenesis.

Said compounds may also make it possible to depigment and/or lighten bodily hairs, the eyelashes, head hair, and also the lips and/or the nails.

One subject of the invention is thus compounds of formula (I) as follows, for their use for depigmenting, lightening and/or bleaching the skin:

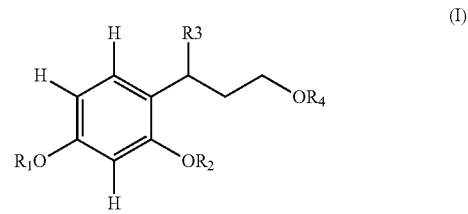

(I)

in which:
$R_1$ and $R_2$, which may be identical or different, denote:
  a) hydrogen,
  b) a radical $COR_5$ in which $R_5$ denotes a linear $C_1$-$C_{10}$ or branched $C_3$-$C_{10}$ alkyl radical, preferably a linear $C_1$-$C_6$ or branched $C_3$-$C_6$ alkyl radical, more preferentially a linear $C_1$-$C_4$ alkyl radical,
$R_3$ denotes a linear $C_1$-$C_6$ or branched $C_3$-$C_6$ alkyl radical, preferably a linear $C_1$-$C_4$ or branched $C_3$-$C_4$ alkyl radical,
$R_4$ denotes:
  a) H,
  b) a linear $C_1$-$C_6$ or branched $C_3$-$C_6$ alkyl radical,
  c) a radical $COR_5$, and also the salts thereof, the solvates thereof and the optical isomers thereof, and the racemates thereof, alone or as a mixture.

Preferably, $R_1$ and $R_2$ are identical.

Preferably, $R_4$ denotes H or a linear $C_1$-$C_4$ alkyl radical, a branched $C_3$-$C_4$ alkyl radical or a radical $COR_5$, more preferentially H or a radical $COR_5$.

Preferentially, the compounds of formula (I) are chosen from those for which:

$R_1$ and $R_2$, which may be identical or different, denote H or a $COCH_3$ radical, and preferably $R_1$ and $R_2$ are identical, $R_3$ denotes methyl, ethyl or isopropyl, and $R_4$ denotes H or a $COCH_3$ radical, and also the salts thereof, the solvates thereof and the optical isomers thereof, and the racemates thereof, alone or as a mixture.

More preferentially, the compounds of formula (I) are such that:

$R_1$ and $R_2$, which may be identical or different, denote H or a $COCH_3$ radical, and preferably $R_1$ and $R_2$ are identical, $R_3$ denotes methyl, and $R_4$ denotes H or a $COCH_3$ radical, and also the salts thereof, the solvates thereof and the optical isomers thereof, and the racemates thereof.

Still within the context of the present invention, the salts of the compounds of formula (I) as defined below comprise the conventional nontoxic salts of said compounds such as those formed from acid or base.

As salts of the compound of formula (I), mention may be made of:

the salts obtained by addition of the compound of formula (I) (when it comprises an acid group) to a mineral base, such as sodium hydroxide, potassium hydroxide, calcium hydroxide, ammonium hydroxide, magnesium hydroxide, lithium hydroxide, and sodium, potassium or calcium carbonate or hydrogen carbonate, for example;

or to an organic base such as a primary, secondary or tertiary alkylamine, for example triethylamine or butylamine. This primary, secondary or tertiary alkylamine may comprise one or more nitrogen and/or oxygen atoms and may thus comprise, for example, one or more alcohol functions; mention may be made in particular of 2-amino-2-methylpropanol, ethanolamine, triethanolamine, 2-dimethylaminopropanol, 2-amino-2-(hydroxymethyl)-1,3-propanediol and 3-(dimethylamino)propylamine.

Mention may also be made of the salts of amino acids, for instance lysine, arginine, guanidine, glutamic acid and aspartic acid. Advantageously, the salts of the compounds of formula (I) (when it comprises an acid group) may be chosen from alkali metal or alkaline-earth metal salts such as sodium, potassium, calcium or magnesium salts; ammonium salts.

The acceptable solvates of the compounds described in the present invention comprise conventional solvates such as those formed during the preparation of said compounds owing to the presence of solvents. Examples that may be mentioned include solvates due to the presence of water or of linear or branched alcohols, such as ethanol or isopropanol.

The optical isomers are especially enantiomers and diastereoisomers.

Still in the context of the present invention:

Unless otherwise indicated, a "$(C_x$-$C_y)$alkyl group" denotes a saturated linear alkyl group comprising from x to y carbon atoms.

Preferentially, the linear saturated or branched alkyl groups may be chosen from methyl, ethyl, propyl, isopropyl, butyl, isobutyl, tert-butyl, pentyl and hexyl.

The compounds of formula (I) that are particularly preferred are chosen from:

| Structure | Compound No. | Chemical name |
|---|---|---|
| 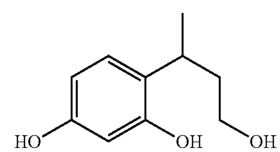 | 1 | 4-(3-hydroxy-1-methylpropyl)benzene-1,3-diol |
| 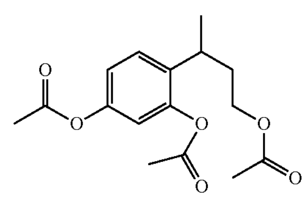 [SMILES: CC(=O)OCCC(C)c1ccc(OC(C)=O)cc1OC(C)=O] | 2 | 4-[4-(acetyloxy)but-2-yl]benzene-1,3-diyl diacetate |
| | 3 | 3-(2,4-dihydroxyphenyl)butyl acetate | and also the salts thereof, the solvates thereof and the optical isomers thereof, and the racemates thereof, alone or as a mixture.

The compounds of formula (I) are novel and constitute another subject of the invention, as do the compositions, in particular the cosmetic compositions, which contain them.

The compounds of the invention of formula (I) may be prepared according to scheme 1 below.

Scheme 1

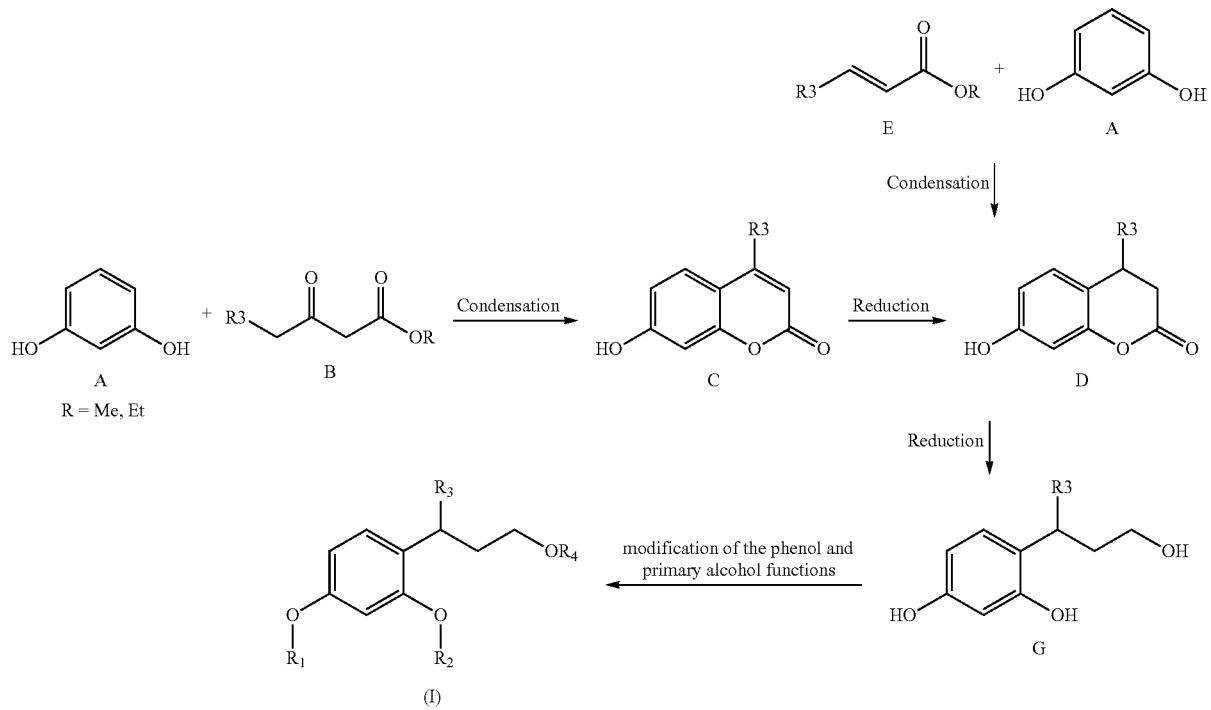

According to this scheme 1, the synthesis of compounds (I) proceeds via the key intermediate of dihydrocoumarin type D, the synthesis of which is described, inter alia, in WO 2005/085 169. A person skilled in the art can adapt the strategy therefrom as a function of the groups R3.

Resorcinol A can react in the presence of a beta-keto ester B to give the coumarin C. This coumarin is reduced by catalytic hydrogenation under the conditions known to those skilled in the art to give D.

D may also be obtained from resorcinol A in the presence of an alpha,beta-unsaturated ester E. The lactone function of D is then reduced with hydrides, after optional prior modifications of the phenol functions via reactions known to those skilled in the art such as protection/deprotection reactions.

Production of the derivatives C and D via reaction between (A and B) or (A and E) may be performed especially in the presence of an organic solvent that may be chosen from toluene, tetrahydrofuran, heptane, isooctane, methyltetrahydrofuran, methyl ethyl ketone, methyl isobutyl ketone, dioxane, ethyl acetate, isopropyl acetate and isododecane, and mixtures thereof, especially at a temperature of between 15 and 200° C., optionally in the presence of a catalyst (acidic or basic) as described in the publications: Synthesis of 7-hydroxycoumarins by Pechmann reaction using Nafion resin/silica nanocomposites as catalysts: Laufer M. C., Hausmann H., Hölderich W. F., J. of Catalysis, 2003, 218, 315-320; Synthesis of 7-hydroxycoumarins catalysed by solid acid catalysts: Hoefnagel A., Gunnewegh E., Downing R., van Bekkum H., J. Chem. Soc. Chem. Commun., 1995, 225-226; derivatives C and D may thus be obtained in particular in the presence of an acid catalyst such as sulfuric acid, methanesulfonic acid, triflic acid or para-toluenesulfonic acid, sulfonic resins such as Dowex® or Amberlyst® resins (sold by the company Aldrich).

The compounds of formula (I) for which $R_1$ and/or $R_2$ denote a group $COR_5$ may be obtained by acetylation/esterification. The acetylation/esterification reaction may be performed with acetic anhydride when $R_5$ denotes a methyl radical (or more generally an anhydride $R_5COOCOR_5$) or acetyl chloride when $R_5$ denotes a methyl radical (or more generally an acid chloride R5COCl), especially in the presence of an aprotic solvent such as toluene, pyridine or tetrahydrofuran. The acetylation/esterification reaction may be selective by using protecting groups on the functions are not to be acetylated/esterified and by performing a deprotection reaction after acetylation/esterification, according to the known techniques of organic synthesis.

The reaction for reduction of the lactone D with hydrides to give the derivative G may optionally be performed in the presence of an aprotic organic solvent, especially tetrahydrofuran, dioxane, dimethylformamide, dimethyl sulfoxide, 2-methyltetrahydrofuran, dichloromethane or toluene, at a temperature of between 0° C. and 200° C., especially between 20° C. and 60° C.

All of these steps may also involve protection/deprotection strategies usually used in organic chemistry and compiled in the publication "Protecting Groups in Organic Synthesis" Greene, Wuts, Wiley Interscience, as a function of the nature of the radicals, so as to selectively place the groups R1, R2 and/or R4 as defined previously using compound G.

By way of illustration of the above general synthetic scheme, it is possible, for example, to synthesize the compounds of formula (I) for which R1=R2=R4=H and R3=methyl, or, respectively, R3=ethyl) according to scheme 2 or 4 (or, respectively, according to scheme 3) below:

In these schemes, "rt" means room temperature.

Scheme 2

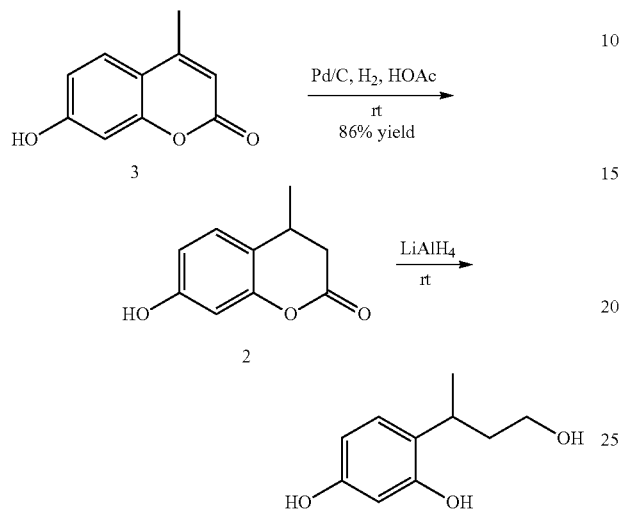

Compound 3 (7-hydroxy-4-methylcoumarin) is commercially available.

Scheme 3

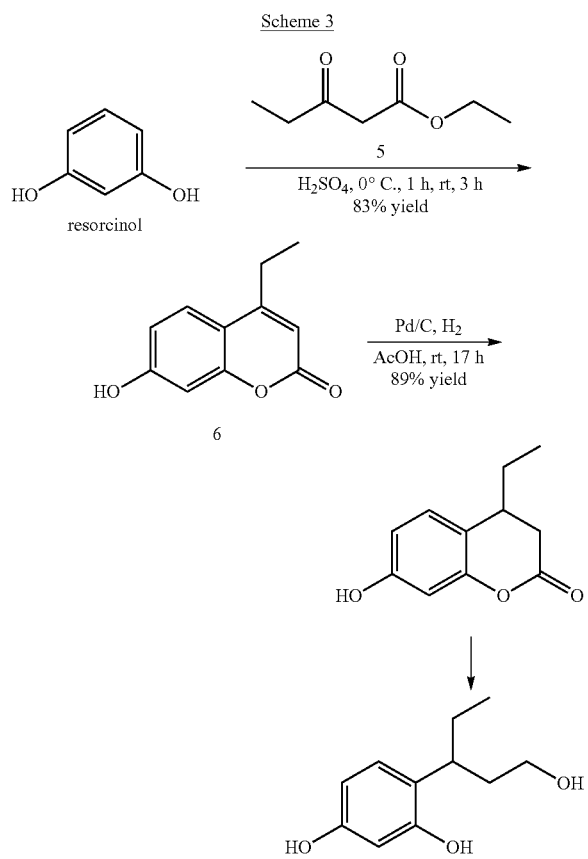

According to scheme 3, the reagents ethyl propionylacetate 5 and resorcinol react as in scheme 1 above to give compound 6, which may be reduced with hydrides to give the corresponding compound of formula (I). A description of this chemistry may be found in the following document: Asian Journal of Chemistry, 2010, 22 (7), 5694-5698.

Scheme 4

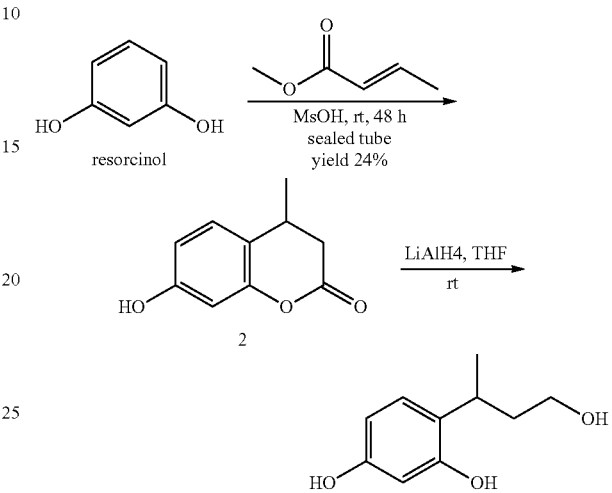

According to scheme 4, resorcinol is reacted with crotonic methyl ester in the presence of excess MSOH to give 7-hydroxy-4-methyl-3,4-dihydrocoumarin 2, which, after reduction with hydrides, gives the corresponding compound of formula (I).

The compounds of formula (I) according to the invention find a most particular application in the cosmetic field.

The composition according to the invention comprises, in a physiologically acceptable medium, a compound of formula (I) as described previously.

The term "physiologically acceptable medium" means a medium that is compatible with human keratin materials such as bodily or facial skin, the lips, mucous membranes, the eyelashes, the nails, the scalp and/or the hair.

Compound (I) may be present in the composition according to the invention in an amount that may be between 0.01% and 10% by weight, preferably between 0.1% to 5% by weight, especially from 0.5% to 3% by weight, relative to the total weight of the composition.

The composition according to the invention is advantageously a cosmetic composition: it may comprise adjuvants usually used in the cosmetic field.

Mention may be made especially of water; organic solvents, especially C2-C6 alcohols; oils, especially hydrocarbon-based oils and silicone oils; waxes, pigments, fillers, dyes, surfactants, emulsifiers; cosmetic active agents, UV-screening agents, polymers, thickeners, preserving agents, fragrances, bactericides, ceramides, odor absorbers, antioxidants.

These optional cosmetic adjuvants may be present in the composition in a proportion of from 0.001% to 80% by weight and especially from 0.1% to 40% by weight relative to the total weight of the composition. In any case, these adjuvants, and the proportions thereof, will be chosen by those skilled in the art such that the advantageous properties of the compounds according to the invention are not, or are not substantially, adversely affected by the envisaged addition.

As active agents, it will be advantageous to introduce into the composition according to the invention at least one compound chosen from: desquamating agents; calmatives, organic or mineral photoprotective agents, moisturizers; depigmenting agents; anti-glycation agents; NO-synthase inhibitors; agents for stimulating the synthesis of dermal or epidermal macromolecules and/or for preventing their degradation; agents for stimulating fibroblast and/or keratinocyte proliferation or for stimulating keratinocyte differentiation; muscle relaxants and/or dermo-decontracting agents; tensioning agents; anti-pollution agents and/or free-radical scavengers; agents acting on the capillary circulation; agents acting on the energy metabolism of cells; and mixtures thereof.

The composition according to the invention may be in any presentation form normally used in the cosmetic field, and especially in the form of an aqueous or aqueous-alcoholic solution, which is optionally gelled, a dispersion of the lotion type, which is optionally a two-phase lotion, an oil-in-water or water-in-oil or multiple (for example W/O/W or O/W/O) emulsion, an aqueous gel, a dispersion of oil in an aqueous phase by means of spherules, these spherules possibly being polymer nanoparticles such as nanospheres and nanocapsules or, better still, lipid vesicles of the ionic and/or nonionic type; aqueous or oily gels. These compositions are prepared according to the usual methods. A composition in the form of an emulsion, in particular an oil-in-water emulsion, is preferably used according to this invention.

The composition according to the invention may constitute a skincare composition, and especially a cleansing, protecting, treating or care cream for the face, the hands, the feet, the major anatomical folds or the body (for example day creams, night creams, makeup-removing creams, foundation creams or antisun creams); a fluid foundation, a makeup-removing milk, a protective or care body milk or an antisun milk; a skincare lotion, gel or mousse, such as a cleansing lotion.

The invention is illustrated in greater detail by the following nonlimiting examples.

EXAMPLE 1

Synthesis of Compound 1

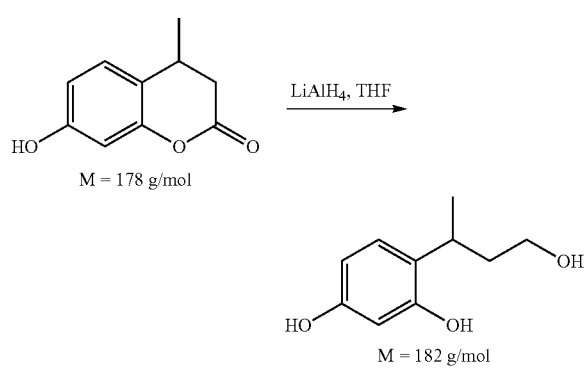

Reagents:
7-hydroxy-4-methyl-3,4-dihydro-2H-1-benzopyran-2-one: 5.7 g
LiAlH4 powder (3 eq): 3.7 g
anhydrous THF: 250 ml Procedure:
The LiAlH4 and the THF (part) were placed in a round-bottomed flask, and coumarin in solution was then added dropwise. The mixture was stirred overnight at room temperature.

The reaction medium was cooled to 0° C. and 20 ml of water and then 250 ml of 1N HCl were added cautiously. The THF was evaporated off and the residue was then extracted three times with diethyl ether. The combined organic phases were washed with saturated NaCl solution and then dried with Na2SO4, filtered and evaporated.

5 g of a slightly pinkish powder corresponding to the expected compound (86% yield) were recovered.

The 1H NMR and mass spectra are in accordance with the structure.

Melting point: 128.8-129.4° C. (capillary tube)

EXAMPLE 2

Synthesis of Compound 2

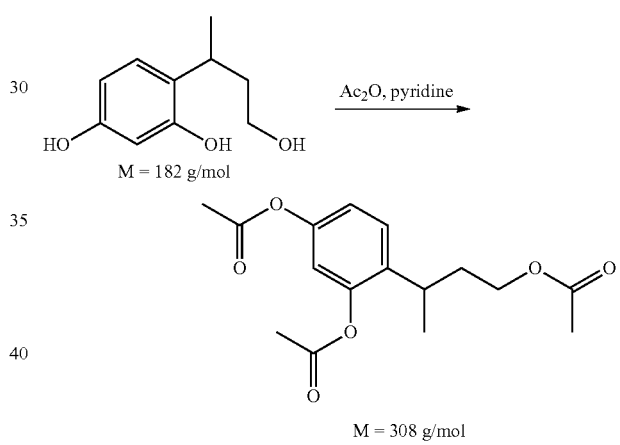

Reagents:
4-(4-hydroxybut-2-yl)benzene-1,3-diol: 0.8 g
acetic anhydride (3 eq): 1.2 ml
pyridine: 5 ml Procedure:
4-(4-Hydroxybut-2-yl)benzene-1,3-diol and then pyridine were placed in a round-bottomed flask. The medium was cooled to 0° C. and acetic anhydride was then added. The mixture was stirred overnight at room temperature.

50 ml of ethyl acetate and 50 ml of 1N HCl were added. The organic phase was washed with twice 50 ml of 1N HCl and then 50 ml of water and 50 ml of saturated NaCl solution. The organic phase was dried with Na2SO4, filtered and evaporated.

1 g of a yellow oil corresponding to the expected compound (77% yield) was recovered.

The 1H NMR and mass spectra are in accordance with the structure.

EXAMPLE 3

Synthesis of Compound 3

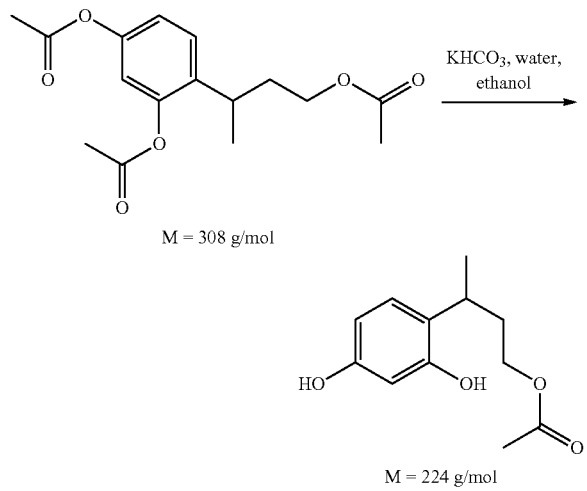

M = 308 g/mol

M = 224 g/mol

Reagents:
4-[4-(acetyloxy)but-2-yl]benzene-1,3-diyldiacetate: 0.4 g
potassium hydrogen carbonate (2 eq): 260 mg
water: 1 ml
ethanol: 2 ml Procedure: 4-[4-(Acetyloxy)but-2-yl]benzene-1,3-diyl diacetate and ethanol were placed in a round-bottomed flask, and water and KHCO3 were then added.

The mixture was left for 1 hour at room temperature. The ethanol was evaporated off and the residue was extracted with ethyl acetate. The organic phase was dried with Na2SO4 and then filtered and evaporated.

0.25 g of a yellow oil corresponding to the expected compound (86% yield) was recovered.

The 1H NMR and mass spectra are in accordance with the expected structure.

EXAMPLE 4

Demonstration of the Activity on Constitutive Melanogenesis

The efficacy was demonstrated on the basis of the following test:

For the evaluations of the effect of preventing or decreasing pigmentation of the skin and/or of lightening of this skin, the examples are performed in the following manner.

The measurement of the depigmenting activity (reduction of melanin production) of compounds of formula (I) was performed by assaying normal human melanocytes in vitro as follows.

First of all, normal human melanocytes were cultured and dispensed into 384 wells. After 24 hours, the culture medium was replaced with a medium containing compounds of formula (I) to be evaluated. The cells were incubated for 72 hours before measurement of the final optical density, which measures the amount of melanin produced by the melanocytes. A dose effect was performed using a wide concentration range of the compounds evaluated. Thus, by making the concentrations and the melanin measurements correspond, it was possible to determine an IC50 in μM: concentration at which a 50% decrease in melanin synthesis is achieved.

The compounds of formula (I) showed a strong depigmenting effect.

| Compound No. | IC50 (μM) | Maximum concentration tested (μM) |
| --- | --- | --- |
| 1 | 3.61 | 200 |
| 2 | 4.08 | 200 |
| 3 | 4.96 | 200 |

These results were compared with those obtained with the closest compound described in the prior art, in patent JP 2007186445 from Kuraray

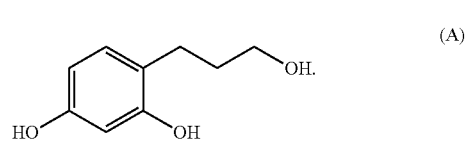 [SMILES: OCCCc1ccc(O)cc1O]

(A)

For this compound (A), the IC50 value is 23.4 μM: maximum concentration tested 200 μM.

The compounds of the invention have melanogenesis-reducing activity that is much greater than that of the compound (A) outside the invention.

EXAMPLE 5

Cosmetic Composition

A skin depigmenting composition is prepared, comprising (in grams):

| | |
| --- | --- |
| Compound 1 | 2 g |
| PEG400 | 68 g |
| Ethanol | 30 g |

The composition applied to the skin makes it possible to attenuate brown spots.

EXAMPLE 6

Gel

A skin depigmenting gel is prepared, comprising (% by weight):

| | |
| --- | --- |
| Compound 2 | 0.25% |
| Carbomer (Carbopol 981 from Lubrizol) | 1% |
| preserving agent | qs |
| Water | qs 100% |

The composition applied to the skin makes it possible to attenuate brown spots.

EXAMPLE 7

Demonstration of the Depigmenting Activity on a Pigmented Reconstructed Epidermis The aim of this test is to evaluate the modulation of melanogenesis in pigmented reconstructed epidermides after "systemic" application of the products.

The compounds are tested at 30 μM in DMSO.

The pigmented epidermides are reconstructed using keratinocytes and melanocytes of European origin seeded on the substrate BPER (Episkin). The test products are added to the culture medium immediately on seeding the cells and at all the changes of medium.

The pigmented reconstructed epidermis standard study model was published by:

Regnier M., Duval C., Galey J. B., Philippe M., Lagrange A., Tuloup R., Schmidt R., Cellular and Molecular Biology, 1999, 45, 7, 969-980: "Keratinocyte-melanocyte co-cultures and pigmented reconstructed human epidermis: models to study modulation of melanogenesis".

The melanin was quantified by image analysis on histological sections after revelation with Fontana-Masson stain. Each stained epidermis is photographed over its entire length using a camera connected to a microscope.

The results are collated in the following table:

The decrease in the amount of melanin is evaluated relative to the solvent (DMSO)

|  | Depigmenting activity/DMSO |
| --- | --- |
| Lucinol | −41% |
| Compound 1 | −59% |

The results obtained show that compound 1 according to the invention has greater depigmenting activity than that of lucinol.

The invention claimed is:

1. A compound for depigmenting, lightening, and/or bleaching the skin, according to formula (I) below:

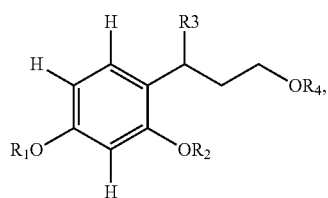

(I)

wherein:
$R_1$ and $R_2$, which may be identical or different, are chosen from:
a) hydrogen, or
b) a radical $COR_5$, wherein $R_5$ is chosen from a linear $C_1$-$C_{10}$ or branched $C_3$-$C_{10}$ alkyl radical;
$R_3$ is chosen from a linear $C_1$-$C_6$ or branched $C_3$-$C_6$ alkyl radical; and
$R_4$ is chosen from:
a) hydrogen,
b) a linear $C_1$-$C_6$ or branched $C_3$-$C_6$ alkyl radical, or
c) a radical $COR_5$,
or a salt thereof, a solvate thereof, an optical isomer thereof, a racemate thereof, or a mixture thereof.

2. The compound according to claim 1, wherein:
$R_1$ and $R_2$, which may be identical or different, are chosen from a radical $COR_5$, wherein $R_5$ is chosen from a linear $C_1$-$C_6$ or branched $C_3$-$C_6$ alkyl radical; and
$R_3$ is chosen from a linear $C_1$-$C_4$ or branched $C_3$-$C_4$ alkyl radical.

3. The compound according to claim 1, wherein $R_1$ and $R_2$, which may be identical or different, are chosen from a radical $COR_5$, wherein $R_5$ is chosen from a linear $C_1$-$C_4$ alkyl radical.

4. The compound according to claim 1, wherein $R_4$ is chosen from hydrogen, a linear $C_1$-$C_4$ alkyl radical, a branched $C_3$-$C_4$ alkyl radical, or a radical $COR_5$.

5. The compound according to claim 1, wherein $R_4$ is chosen from hydrogen or a radical $COR_5$.

6. The compound according to claim 1, wherein:
$R_1$ and $R_2$, which may be identical or different, are chosen from hydrogen or a $COCH_3$ radical;
$R_3$ is chosen from methyl, ethyl or isopropyl; and
$R_4$ is chosen from hydrogen or a $COCH_3$ radical,
or a salt thereof, a solvate thereof, an optical isomer thereof, a racemate thereof.

7. The compound according to claim 1, wherein:
$R_1$ and $R_2$, which may be identical or different, are chosen from hydrogen or a $COCH_3$ radical;
$R_3$ is methyl; and
$R_4$ is chosen from hydrogen or a $COCH_3$ radical,
or a salt thereof, a solvate thereof, an optical isomer thereof, or a racemate thereof.

8. The compound according to claim 1, wherein the compound is chosen from:

| Structure | Compound No. | Chemical name |
| --- | --- | --- |
| 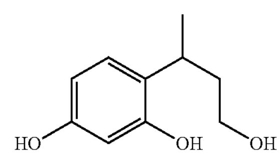 | 1 | 4-(3-hydroxy-1-methylpropyl)benzene-1,3-diol |
| 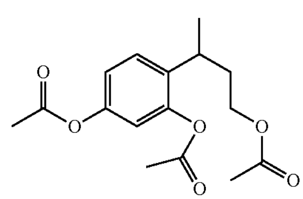 [SMILES: CC(=O)OCCC(C)c1ccc(OC(C)=O)cc1OC(C)=O] | 2 | 4-[4-(acetyloxy)but-2-yl]benzene-1,3-diyl diacetate |
|  | 3 | 3-(2,4-dihydroxyphenyl)butyl acetate | or salts thereof, solvates thereof, optical isomers thereof, racemates thereof, or mixtures thereof.

9. A cosmetic composition comprising, in a physiologically acceptable medium, at least one compound according to formula (I) below:

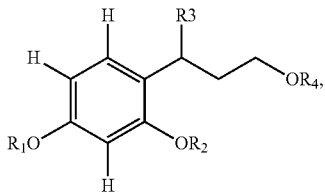

wherein:
R$_1$ and R$_2$, which may be identical or different, are chosen from:
a) hydrogen, or
b) a radical COR$_5$, wherein R$_5$ is chosen from a linear C$_1$-C$_{10}$ or branched C$_3$-C$_{10}$ alkyl radical;
R$_3$ is chosen from a linear C$_1$-C$_6$ or branched C$_3$-C$_6$ alkyl radical; and
R$_4$ is chosen from
a) hydrogen,
b) a linear C$_1$-C$_6$ or branched C$_3$-C$_6$ alkyl radical, or
c) a radical COR$_5$,
or a salt thereof, a solvate thereof, an optical isomer thereof, a racemate thereof, or a mixture thereof.

10. The composition according to claim 9, wherein:
R$_1$ and R$_2$, which may be identical or different, are chosen from hydrogen or a radical COR$_5$, wherein R$_5$ is chosen from a linear C$_1$-C$_6$ or branched C$_3$-C$_6$ alkyl radical; and
R$_3$ is chosen from a linear C$_1$-C$_4$ or branched C$_3$-C$_4$ alkyl radical.

11. The composition according to claim 9, wherein R$_1$ and R$_2$, which may be identical or different, are chosen from a radical COR$_5$, wherein R$_5$ is chosen from a linear C$_1$-C$_4$ alkyl radical.

12. The composition according to claim 9, wherein R$_4$ is chosen from hydrogen, a linear C$_1$-C$_4$ alkyl radical, a branched C$_3$-C$_4$ alkyl radical, or a radical COR$_5$.

13. The composition according to claim 9, wherein R$_4$ is chosen from hydrogen or a radical COR$_5$.

14. The composition according to claim 9, comprising at least one compound according to formula (I) wherein:
R$_1$ and R$_2$, which may be identical or different, are chosen from hydrogen or a COCH$_3$ radical;
R$_3$ is chosen from methyl, ethyl or isopropyl; and
R$_4$ is chosen from hydrogen or a COCH$_3$ radical,
or a salt thereof, a solvate thereof, an optical isomer thereof, a racemate thereof, or a mixture thereof.

15. The composition according to claim 9, comprising at least one compound according to formula (I) wherein:
R$_1$ and R$_2$, which may be identical or different, are chosen from hydrogen or a COCH$_3$ radical;
R$_3$ is methyl; and
R$_4$ is chosen from hydrogen or a COCH$_3$ radical,
or a salt thereof, a solvate thereof, an optical isomer thereof, a racemate thereof, or a mixture thereof.

16. The composition according to claim 9, wherein the composition comprises at least one compound chosen from:

| Structure | Compound No. | Chemical name |
|---|---|---|
| 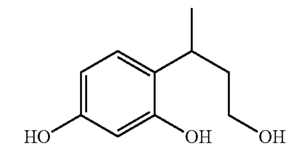 | 1 | 4-(3-hydroxy-1-methylpropyl)benzene-1,3-diol |
| 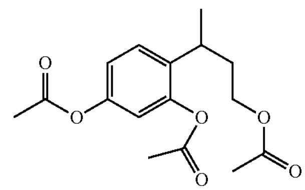 [SMILES: CC(=O)OCCC(C)c1ccc(OC(C)=O)cc1OC(C)=O] | 2 | 4-[4-(acetyloxy)but-2-yl]benzene-1,3-diyl diacetate |
|  | 3 | 3-(2,4-dihydroxyphenyl)butyl acetate | or a salt thereof, a solvate thereof, an optical isomer thereof, a racemate thereof, or a mixture thereof.

17. The composition according to claim 9, wherein the at least one compound according to formula (I) is present in an amount ranging from about 0.01% to about 10% by weight, relative to the total weight of the composition.

18. The composition according to claim 9, wherein the at least one compound according to formula (I) is present in an amount ranging from about 0.1% to about 5% by weight, relative to the total weight of the composition.

19. The composition according to claim 9, wherein the at least one compound according to formula (I) is present in an amount ranging from about 0.5% to about 3% by weight, relative to the total weight of the composition.

20. A nontherapeutic cosmetic process for depigmenting, lightening and/or bleaching keratin materials, wherein the method comprises applying to the keratin materials a cosmetic composition, the cosmetic composition comprising, in a physiologically acceptable medium, at least one compound according to formula (I) below:

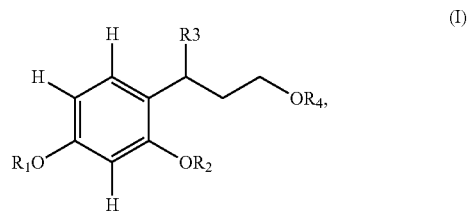

wherein:
R$_1$ and R$_2$, which may be identical or different, are chosen from:
a) hydrogen, or
b) a radical COR$_5$, wherein R$_5$ is chosen from a linear C$_1$-C$_{10}$ or branched C$_3$-C$_{10}$ alkyl radical;

$R_3$ is chosen from a linear $C_1$-$C_6$ or branched $C_3$-$C_6$ alkyl radical; and $R_4$ is chosen from a) hydrogen,
b) a linear $C_1$-$C_6$ or branched $C_3$-$C_6$ alkyl radical, or
c) a radical $COR_5$, or a salt thereof, a solvate thereof, an optical isomer thereof, a racemate thereof, or a mixture thereof.

* * * * *